(12) United States Patent
Schwammberger et al.

(10) Patent No.: US 9,532,818 B2
(45) Date of Patent: Jan. 3, 2017

(54) ORTHOPEDIC NAIL AND AN ORTHOPEDIC NAIL SYSTEM

(75) Inventors: Andreas E. Schwammberger, Niederdorf (CH); Jordan Velikov, Horgen (CH); Rolf Dittmann, Nussbaumen (CH)

(73) Assignee: Zimmer GmbH, Winterthur (CH)

( * ) Notice: Subject to any disclaimer, the term of this patent is extended or adjusted under 35 U.S.C. 154(b) by 50 days.

(21) Appl. No.: 13/501,644

(22) PCT Filed: Oct. 12, 2010

(86) PCT No.: PCT/EP2010/006216
§ 371 (c)(1),
(2), (4) Date: Jun. 29, 2012

(87) PCT Pub. No.: WO2011/045025
PCT Pub. Date: Apr. 21, 2011

(65) Prior Publication Data
US 2012/0265202 A1    Oct. 18, 2012

(30) Foreign Application Priority Data

Oct. 13, 2009   (EP) .................. PCT/EP2009/007354

(51) Int. Cl.
*A61B 17/58* (2006.01)
*A61B 17/74* (2006.01)
*A61B 17/72* (2006.01)

(52) U.S. Cl.
CPC ......... *A61B 17/744* (2013.01); *A61B 17/7233* (2013.01)

(58) Field of Classification Search
CPC .............. A61B 17/744; A61B 17/7233; A61B 17/7266; A61B 17/7283
(Continued)

(56) References Cited

U.S. PATENT DOCUMENTS 3,433,220 A * 3/1969 Zickel ............................. 606/67
4,794,919 A * 1/1989 Nilsson ................ A61B 17/744
606/65

(Continued)

FOREIGN PATENT DOCUMENTS

DE   202004018748 U1   2/2005
EP       1016382 A2   7/2000
(Continued)

OTHER PUBLICATIONS

"International Application Serial No. PCT/EP2009/007354, International Preliminary Report on Patentability mailed Sep. 29, 2010", 8 pgs.

(Continued)

*Primary Examiner* — Jan Christopher Merene
(74) *Attorney, Agent, or Firm* — Schwegman Lundberg & Woessner, P.A.

(57) ABSTRACT

An orthopedic nail of generally rod-like shape having a through hole extending from a first side to a second side of the orthopedic nail and being adapted to receive a screw and/or a pin, a first end of the through hole at the first side defining a rim region, wherein at least one surface notch is provided in the rim region at and restricted to an outer circumferential surface of the orthopedic nail, the surface notch being arranged transverse to a nail axis of the orthopedic nail, a width (W) of the surface notch in the direction of the nail axis being smaller than a diameter of the through hole.

16 Claims, 6 Drawing Sheets

Figure 1:
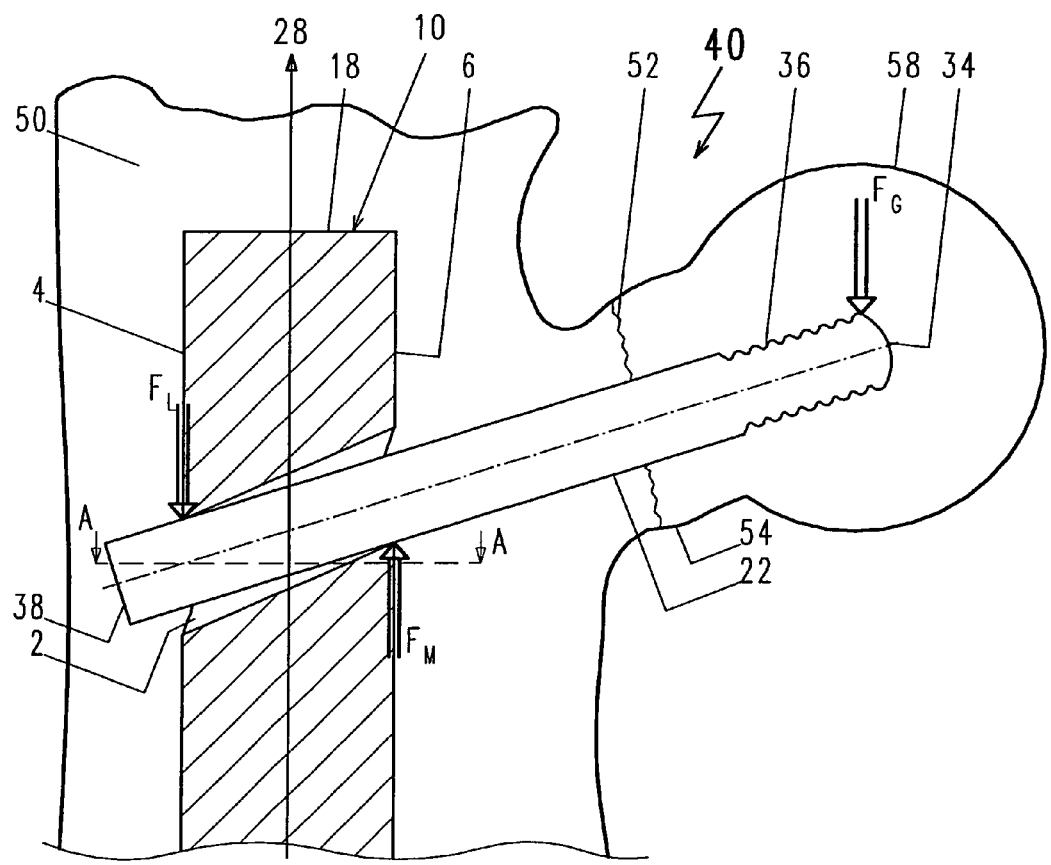
Figure 1:
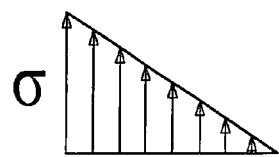

(58) Field of Classification Search
USPC .................. 606/62–68, 289–290, 295–296
See application file for complete search history.

(56) References Cited

U.S. PATENT DOCUMENTS

| | | | |
|---|---|---|---|
| 5,454,813 A * | 10/1995 | Lawes .............................. | 606/62 |
| 5,658,288 A * | 8/1997 | Kim ................................ | 606/64 |
| 5,741,256 A | 4/1998 | Bresina | |
| 6,168,595 B1 * | 1/2001 | Durham et al. ................ | 606/64 |
| 6,808,527 B2 * | 10/2004 | Lower et al. ................... | 606/62 |
| 7,247,157 B2 * | 7/2007 | Prager et al. ................... | 606/64 |
| 7,608,075 B2 * | 10/2009 | Tornier ........................... | 606/64 |
| 7,763,023 B2 * | 7/2010 | Gotfried ......................... | 606/64 |
| 7,850,690 B2 * | 12/2010 | Frigg et al. .................... | 606/67 |
| 8,353,910 B2 * | 1/2013 | Dell'Oca ........................ | 606/64 |
| 8,668,695 B2 * | 3/2014 | Schwammberger et al. ... | 606/67 |
| 2004/0172027 A1 | 9/2004 | Speitling et al. | |
| 2005/0165395 A1 * | 7/2005 | Orbay ................ A61B 17/8061 | 606/60 |
| 2005/0182406 A1 * | 8/2005 | Orbay ................ A61B 17/8047 | 606/32 |
| 2006/0084999 A1 * | 4/2006 | Aschmann ...................... | 606/64 |
| 2008/0051790 A1 * | 2/2008 | Defossez ............. A61B 17/744 | 606/64 |
| 2008/0262498 A1 * | 10/2008 | Fernandez Dell'Oca ...... | 606/65 |
| 2009/0062862 A1 * | 3/2009 | Perrow .............. A61B 17/8047 | 606/280 |
| 2010/0063503 A1 * | 3/2010 | Dell'Oca ........................ | 606/62 |
| 2010/0174284 A1 * | 7/2010 | Schwammberger et al. ... | 606/62 |
| 2010/0179551 A1 * | 7/2010 | Keller et al. ................... | 606/67 |
| 2011/0071575 A1 * | 3/2011 | Bhatnagar .......... A61B 17/8052 | 606/289 |
| 2011/0152945 A1 * | 6/2011 | Matityahu .......... A61B 17/7059 | 606/290 |

FOREIGN PATENT DOCUMENTS

| | | |
|---|---|---|
| EP | 1452144 A2 | 9/2004 |
| GB | 2209947 A | 6/1989 |
| WO | WO-2007038560 A1 | 4/2007 |
| WO | WO-2008147975 A1 | 12/2008 |
| WO | WO-2011045025 A1 | 4/2011 |

OTHER PUBLICATIONS

"International Application Serial No. PCT/EP2009/007354, International Search Report mailed Feb. 10, 2010", 4 pgs.

"International Application Serial No. PCT/EP2009/007354, Written Opinion Mailed Feb. 10, 2010", 5 pgs.

"International Application Serial No. PCT/EP2010/006216, International Preliminary Report on Patentability mailed Apr. 17, 2012", 6 pgs.

"International Application Serial No. PCT/EP2010/006216, International Search Report mailed Mar. 16, 2011", 4 pgs.

"International Application Serial No. PCT/EP2010/006216, Written Opinion mailed Mar. 16, 2011", 5 pgs.

\* cited by examiner

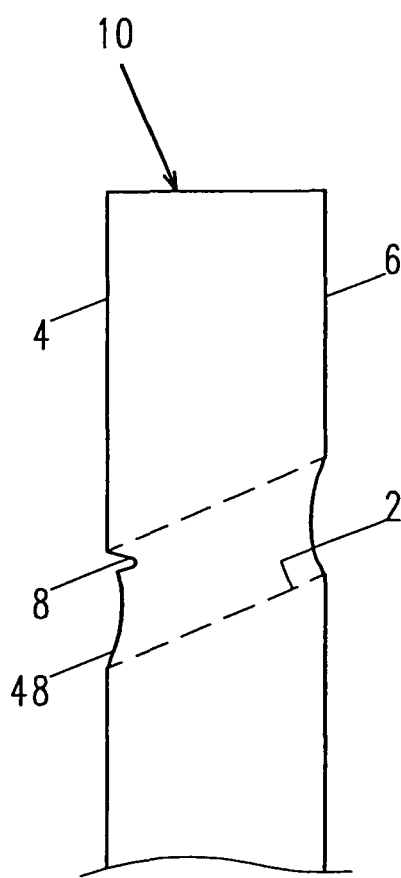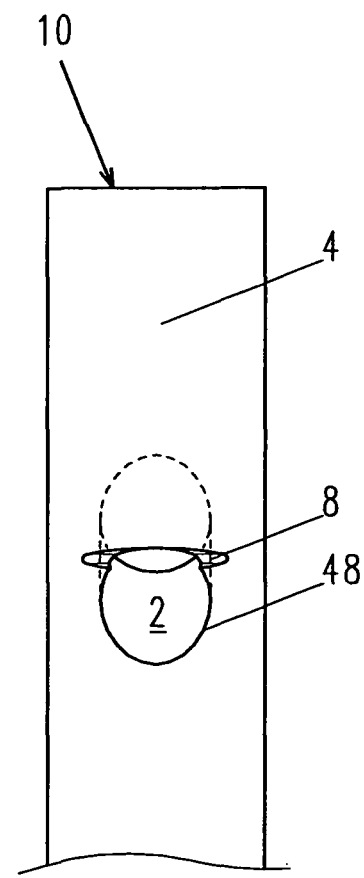
Fig. 5a    Fig. 5b
Fig. 5

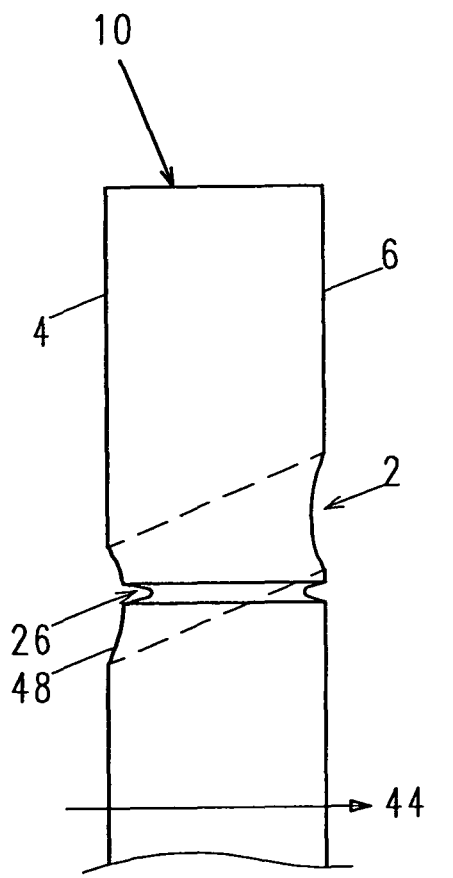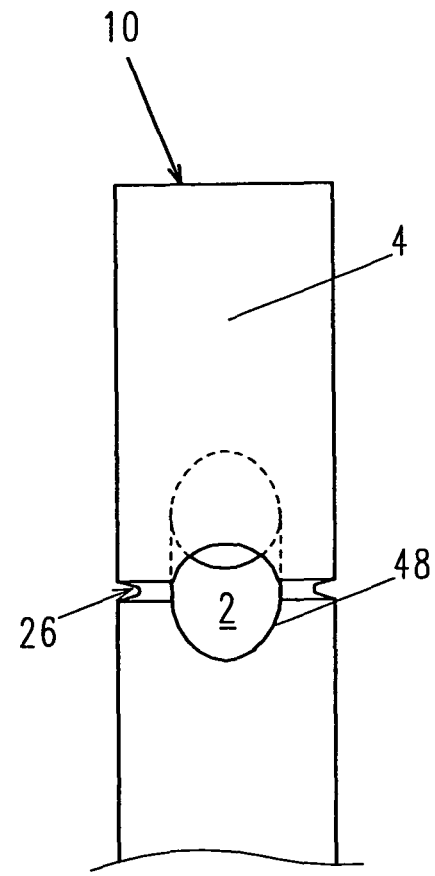
Fig. 6a  Fig. 6b
Fig. 6

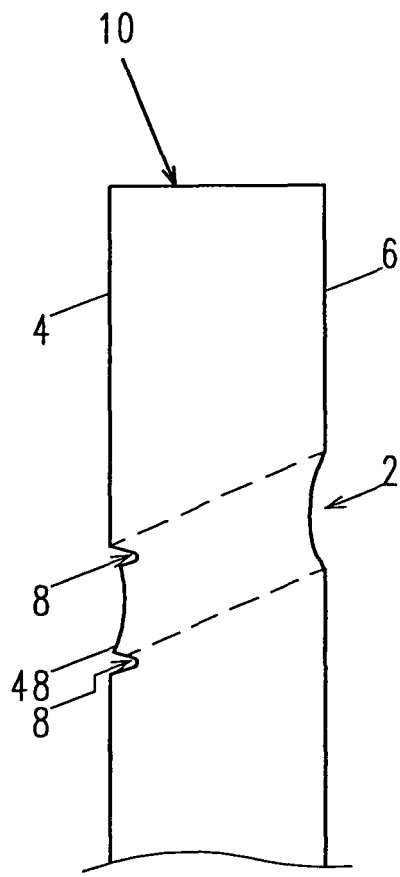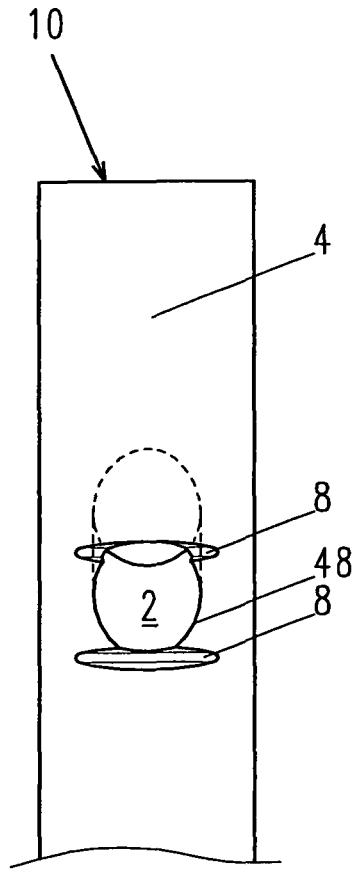
Fig. 7a          Fig. 7b
Fig. 7

ORTHOPEDIC NAIL AND AN ORTHOPEDIC NAIL SYSTEM

This application is a U.S. National Phase Patent Application claiming priority to International Application Serial No. PCT/EP2010/006216 filed on Oct. 12, 2010, entitled "AN ORTHOPEDIC NAIL AND AN ORTHOPEDIC NAIL SYSTEM" which claims priority to International Application Serial No. PCT/EP2009/007354 filed on Oct. 13, 2009, entitled "AN ORTHOPEDIC NAIL AND AN ORTHOPEDIC NAIL SYSTEM", the disclosures of which are hereby explicitly incorporated by reference herein.

The present disclosure relates to an orthopedic nail and an orthopedic nail system, in particular for the treatment of femoral neck fractures.

Intramedullary nails are known for the treatment of fractures of long bones. For example, known femoral nail systems include an intramedullary rod having a geometry adapted to that of the shape of the femoral bone and a lag screw for entering and fixating the femoral head to the main body of the femur should the femoral neck be fractured. The rod comprises a through bore suited for accommodating the lag screw, wherein the bore extends from a lateral and more distal position to a medial and more proximal position in a proximal section of the intramedullary rod. The angle between the rod axis and the through bore axis, defining, in an implanted state, also the lag screw axis, is chosen such that it is as good as possible in agreement with a patient's CCD angle. During surgery, the lag screw is typically fed through the through hole from a lateral side to a medial side of the intramedullary rod to accommodate the lag screw inside the through hole.

As shown in FIG. 1, in such a system, the proximal end of the lag screw is loaded with a force $F_G$. Generally, there is a certain amount clearance between the through hole and the lag screw to enable the lag screw to float axially inside the bore, in particular towards the lateral side, during the healing process. This clearance which leads to the lag screw essentially having two support points in the through hole, which bear the force $F_G$ induced: one support point at the medial side of the intramedullary nail in the distal region of the through hole opening, where the force $F_M$ acts on the lag screw, and a second support point at the lateral side of the intramedullary nail in the proximal region of the through hole opening, where the force $F_L$ acts. This force $F_L$ is amplified by the ratio of the leverage of the lag screw in the through hole. The force $F_M$ generally induces a compressive stress in the massive distal part of the rod. The force $F_L$ induces a tensile stress in the region of the through hole. The maximum tension is found in a region of the through hole having a very critical geometry and sharp edges. This, in combination with a notch effect of the through hole in the rod leads to an even worse tension distribution and a maximum tension is found on the lateral side of the through hole, where there is very little material provided to be able to bear this tension.

For this reason, it is known to build intramedullary rods with a very strong material and with a large amount of material in the region of the through hole. This increase of the rod size in the region of the through hole is both demanding in cost and work and also requires an extreme amount of healthy bone and tissue removal on insertion of the orthopedic nail system into the bone. WO 2008/147975 A1 discloses an intramedullary nail with an optimized reinforcement zone around the lateral end of the through hole.

EP 1 452 144 A2 discloses an intramedullary nail having a recess surrounding the lateral end of the through hole such that a flattened rim is provided. This recess has a large volume.

Documents WO 2008/147975 A1 and DE 20 2004 018 748 U1 disclose an intramedullary nail including an elongated body having a transverse bore, wherein the transverse bore includes a substantially cylindrical portion, and slots and a groove, respectively.

One object of this disclosure is to provide a novel orthopedic nail that is able to cope with the above described adverse effects.

Accordingly, the present disclosure provides an orthopedic nail of generally rod-like shape. The orthopedic nail has a through hole. The through hole extends from a first side to a second side of the orthopedic nail. The through hole is adapted to receive a screw and/or a pin. A first end of the through hole at the first side defines a rim region. At least one notch is provided in the rim region. The notch is arranged transverse to a nail axis of the orthopedic nail. A width of the notch in the direction of the nail axis is smaller than a diameter of the through hole.

Accordingly, the present disclosure provides an orthopedic nail of generally and/or at least substantially rod-like shape. The orthopedic nail has a through hole. The through hole extends from a first side to a second side of the orthopedic nail. The through hole is adapted to receive a screw and/or a pin. A first end of the through hole at the first side defines a rim region. At least one surface notch, in particular at least a part thereof, in particular having a notch ground, is provided in the rim region at and restricted to an outer circumferential surface of the orthopaedic nail. In particular, the surface notch is arranged transverse to a nail axis of the orthopedic nail and/or of a proximal portion of the orthopedic nail. A width of the surface notch in the direction of the nail axis is smaller than a diameter of the through hole. In particular, the through hole extends transverse and/or obliquely to the nail axis.

The notch is suited to interrupt a high concentration of tensile stress lines in the rim region at the first side of the orthopedic nail, thereby shifting the high concentration of tensile stress and moving the maximum stress concentration to a location where more material is available. Thereby the rim region at the first side of the orthopedic nail does not have to be reinforced reducing the cost of the orthopedic nail. One advantage here as compared to e.g. EP 1 452 144 A2 is that the bone ingrowth volume is reduced and hence an additional trauma on extraction of the orthopedic nail is considerably reduced.

In an embodiment, the surface notch is provided at and restricted to the outer circumferential surface of the orthopaedic nail, i.e. does not fully extend through the orthopaedic nail.

In an embodiment, when viewed from the first side and/or in a plan view onto the first side, a depth of the surface notch along the viewing direction and terminating in the notch ground is smaller than the diameter of the orthopaedic nail. Thus, the surface notch has a finite depth. The depth of the notch may be smaller than or equal to a half, in particular a third or a fourth or a fifth, of the diameter of the orthopaedic nail. The depth of the notch may be equal to or smaller than 4 mm, in particular 3 mm or 2 mm.

In an embodiment, when viewed from an anterior or posterior side, the depth of the surface notch along the first-side-viewing direction is defined by the distance between the outermost point of the outer circumferential surface of the in particular virtual none-holed orthopaedic nail and the innermost point of the notch ground.

The slots and the groove of documents 2008/147975 A1 and DE 20 2004 018 748 U1, respectively, are not provided to enhance the strength of the intramedullary nail in the region of the transverse bore. When viewed from a side at which an end of the transverse bore is provided, the slots and the groove do not have a ground and, thus, no associated depth along that viewing direction, but instead fully extend through the intramedullary nail. Thus, the surface notch according to the present disclosure is substantially different from the slots and the groove disclosed in documents 2008/147975 A1 and DE 20 2004 018 748 U1, respectively.

In an embodiment, the notch is intersected by and/or superimposed with the first end of the through hole. Depending on its proximal-distal position, the notch may be visible partly only and/or a partly virtual notch. In particular, only an anterior portion and a posterior portion of the notch may be visible, in particular wherein the anterior and posterior portions are not connected to each other but separated by the first end of the through hole, the anterior and posterior portions of the notch being provided at an anterior part of the rim region anterior of a proximal-distal center plane of the through hole and a posterior part of the rim region posterior of the proximal-distal center plane of the through hole.

In a further embodiment, the surface notch and/or the notch ground is of longitudinal shape, a length of the surface notch and/or the notch ground extending, in particular in a transverse plane, tangentially to, in a direction parallel offset to a tangent to or at least partly circumferentially around the outer circumferential surface. The surface notch may be an elongate surface notch. The elongate surface notch may be visible partly only as mentioned above. The surface notch and/or a length of the surface notch may be arranged transverse to a through hole axis of the through hole and/or at a distance from the through hole axis.

In a further embodiment, in a plan view onto the first side, the surface notch exceeds the through hole and/or the rim region in anterior direction and posterior direction.

In a further embodiment, the notch is arranged in parallel to a plane which is substantially perpendicular to the nail axis.

In a further embodiment, the notch is of longitudinal shape and/or a length of the notch is longer than the diameter of the through hole.

In a further embodiment, the notch is arranged substantially perpendicular to a through hole axis of the through hole and/or is arranged substantially perpendicular to the nail axis. A length of the notch may be oriented in anterior-posterior direction of the orthopedic nail. As to a definition of the anterior-posterior direction, it becomes clear to the skilled person, as the nail has a proximal distal direction essentially along its elongation, a lateral-medial direction, essentially defined by a projection of the through bore axes on the nail cross section. The anterior-posterior direction is then defined as being arranged perpendicular to a plane which is spanned by the proximal-distal and the lateral-medial direction.

In a further embodiment, the width of the notch, e.g. the smaller dimension in a plan view onto the notch, is smaller than a radius of the through hole. A depth and/or the width of the notch may be in the range of 1 mm to 4 mm, wherein the lower limit of the range may as well be 1.5 mm and/or the upper limit may as well be 2 mm or 3 mm. The depth and/or the width of the notch may be up to a quarter, in particular up to a sixth or an eighth of the diameter of the through hole.

In an further embodiment, the notch is positioned in a proximal part of the rim region towards a proximal end of the orthopedic nail away from the through hole axis, in particular in a proximal third of the rim region.

In a further embodiment, the notch is provided at a proximal end of the rim region.

In a further embodiment, the notch is groove-shaped and/or a length of the notch has a cross-section which is of substantially rounded shape.

In a further embodiment, the notch is provided distant from a proximal end of the rim region. This might be beneficial, as the lateral support point is thereby not reduced in size and/or manipulated in shape and the above described leverage is not changed.

In a further embodiment, at least two notches are provided in the rim region.

In a further embodiment, a first notch is positioned in a proximal half of the rim region and a second notch is positioned in a distal half of the rim region.

In a further embodiment, a first notch is provided at a proximal end of the rim region and/or a second notch is provided at a distal end of the rim region. Thus, the region of low material strength and/or unfavorable geometry is isolated from the rest of the orthopedic nail which effectively prevents the region of low material strength from being charged with tensile or pressure stress in a direction parallel to the rod axis.

In a further embodiment, the notch is provided as at least one circumferential notch around the circumference of the orthopedic nail, wherein the circumferential notch is provided in a plane that is substantially perpendicular to the nail axis or the circumferential notch is provided in a plane oblique to the nail axis.

In a further embodiment, the orthopedic nail is an intramedullary nail adapted for the use within a bone, in particular a long bone, having a medullary channel.

In a further embodiment, the notch is provided on a lateral side of the orthopedic nail.

In a further embodiment, the surface notch is suited to interrupt tensile stress lines in the rim region induced by a force acting on a support point for the screw and/or pin at the first side in a proximal region of the first end of the through hole.

According to an aspect of the present disclosure, there is provided an orthopedic nail system in particular for the use as a femoral osteosynthetic system which includes an orthopedic nail in accordance with the present disclosure and a screw and/or a pin, wherein the screw and/or pin are adapted to be received in the through hole of the orthopedic nail and are also adapted for the treatment of bone fractures.

It will be appreciated that the specific features of the embodiments described above can be combined. Thus any combinations of the features described in the dependent claims are disclosed herein, be they explicitly mentioned or not.

Further areas of applicability will become apparent from the description provided herein.

Figure 2:
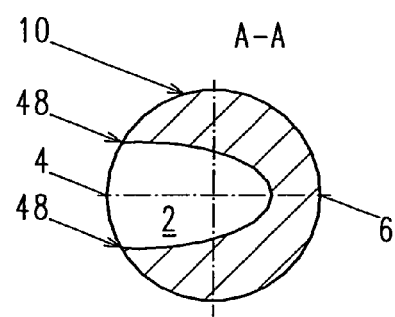
Figure 3:
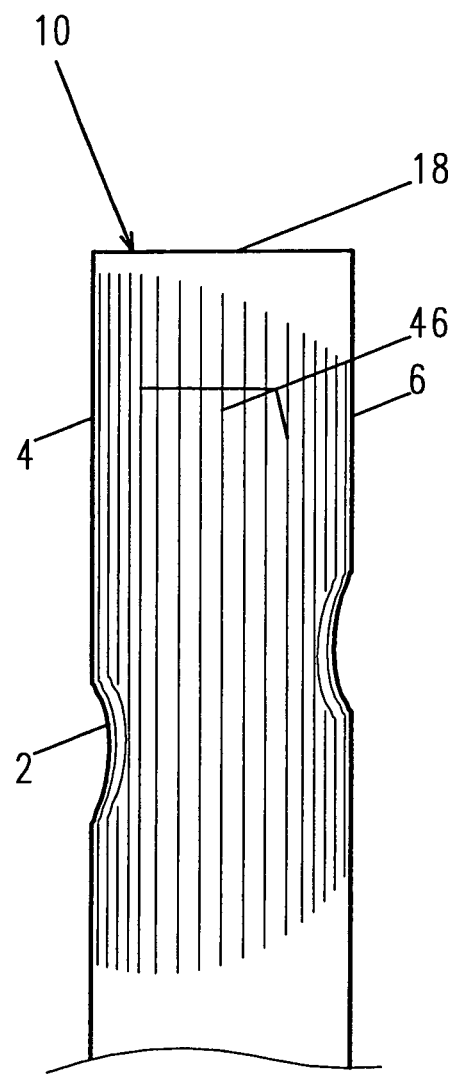
Figures 4, 4A, 4B:
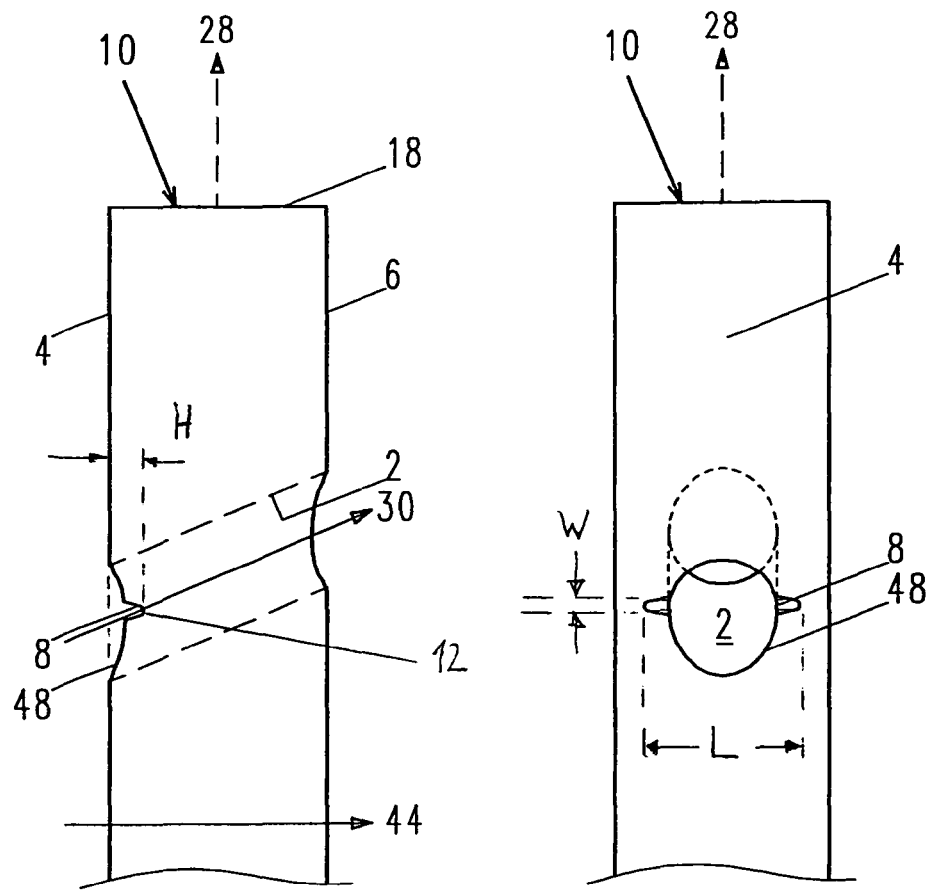

The present disclosure will be explained in more detail and become fully understood from the detailed description and the accompanying drawings, wherein FIG. 1 shows a longitudinal cross-section of an orthopedic nail system including an orthopedic nail according to the prior art, FIG. 2 shows a section along A-A in FIG. 1, FIG. 3 shows a side view of the orthopedic nail in FIG. 1, FIGS. 4a and 4b show an embodiment of an orthopedic nail, FIGS. 5a and 5b show a further embodiment of an orthopedic nail, FIGS. 6a and 6b show a further embodiment of an orthopedic nail, and FIGS. 7a and 7b show a further embodiment of an orthopedic nail.

The following description of the embodiments is merely exemplary in nature and is in no way intended to limit the disclosure, its application, or uses. It should be understood that throughout the drawings, the same reference numerals indicate similar or corresponding parts and features.

FIG. 1 already discussed above shows a fragmentary view of a prior art orthopedic nail system 40 in which the bone nail system or orthopedic nail system 40 is shown implanted into a femur 50. The orthopedic nail system 40 includes an orthopedic nail 10, which is an intramedullary rod or intramedullary nail 10. Also shown is a bone screw 22, which is also known as a lag screw 22. The lag screw 22 has a threaded portion 36 at its proximal end 34, and is typically inserted into the nail 10 from a first, lateral side 4 of the nail 10 through a through hole 2 of the orthopedic nail 10 and projects out of the nail 10 on a second, medial side 6 of the nail 10 into a femoral head 58 where it is subsequently anchored to aid in the treatment of a fracture 52 of a femoral neck 54 of the femur 50.

The through hole 2 is provided in a proximal part of the intramedullary nail 10, with the through hole 2 obliquely extending through the nail 10, wherein the angle between a through hole axis 30 as shown in FIG. 4 and a nail axis 28 is chosen such that it is in agreement with a patient's CCD angle. The lateral end of the through hole 2 is located closer to a distal end of the nail 10 than the medial end of the through hole 2.

The through hole 2 may be a bore and may be produced by drilling the bore 2 into the nail 10. FIG. 1 only shows a proximal part of the nail 10 including a proximal end 18, as the distal part of the nail 10 may vary. Moreover, the type of lag screw 22 used may vary and is by no means limited to the screw 22 depicted in FIG. 1 but it may be any type of screw or pin used in this type of medical application. In particular, a distal end 38 of the lag screw 22 may be of any kind and shape as is typically used in this sort of application.

Arrow $F_G$ indicates a the force acting on the distal end of the lag screw 22 due to loading by the patient's body weight, inducing a momentum on the lag screw through a lever arm at the distal part of the lag screw. Due to the clearance between the lag screw and the bore the lag screw is supported essentially at two support points, one at the medial distal end of the bore where force $F_M$ acts on the lag screw, and at the lateral proximal end of the bore by Force $F_L$, whereby the latter has to provide an equilibrium for the momentum induced by $F_G$, with the medial support point as the pivotal point. While force $F_M$ introduces a compressive stress component in the region of the nail distal from the bore, $F_L$ induces merely tensile stresses in the region of the bore.

An theoretical qualitative distribution of the tensile stresses across the nail 10 due to the force exerted by lag screw 22, leaving any notch effect out of consideration, is shown in the lower part of FIG. 1. As is shown in combination with FIG. 2, which shows a section along line A-A of FIG. 1, the maximum tension is found in a rim region 48 which is defined by the lateral end of the through hole 2 which has a very critical geometry and sharp edges. The rim region 48 confines the lateral end of the through hole 2, i.e. confines the lateral through hole opening.

This tensile stress induces a "flux" of tension which "flux" of tension, due to the effect of the bore, concentrates in the rim region 48 of the through hole 2 and, thus, in a region of very low material strength. FIG. 3 shows schematic "tension flux" lines 46. On both ends of the through hole 2 the flux lines 46 concentrate in the region of the through hole 2, wherein on the lateral side 4 of the orthopedic nail 10 the flux lines 46 combine with the high tensile stress shown in FIG. 1. Thus, the tensile stresses are exaggerated where the lowest material strength is found, i.e. in the rim region 48.

In the following reference is made to FIGS. 4 through 7. It has been found that a transverse notch 8, 26 applied at the rim region 48 at the lateral end of the oblique through hole 2 is suited to interrupt the stress lines at the rim region 48, so as to virtually isolate the edge region of the bore from the tension flux and move the maximum stress concentration to a location where more material is available. Through the notch 8, 26, the region of low material strength and unfavorable geometry is virtually isolated from the tensile stress. In particular, the notch 8, 26 is provided at an outer wall of the orthopedic nail 10. The notch 8, 26 is a surface notch and, thus, is provided in the rim region 48 at and restricted to an outer circumferential surface of the orthopaedic nail 10. The surface notch 8, 26 terminates in a notch ground 12. One advantage here is, as compared to e.g. EP 1 452 144 A2, that the bone ingrowth volume and hence an additional trauma on the subsequent extraction of the nail is considerably reduced, and the extraction of the nail from the patient's body is facilitated.

The notch 8, 26 may be arranged virtually everywhere along the proximal-distal direction on the lateral end of the through hole 2. The notch 8, 26 may be e.g. drilled or milled. The notch 8, 26 will typically have a rounded cross-section, but as the case may be it can also have a triangular cross-section, a rectangular cross-section or any substantially concavely shaped cross-section. The notch 8, 26 can also be described as a groove.

Preferably both a width and a depth of the notch 8, 26 are in a range from 1 mm or 1.5 mm to 2 mm, 3 mm or 4 mm. In particular, the width of the notch 8, 26 corresponds to a dimension of the notch 8, 26 in the direction of the nail axis 28, and the depth of the notch 8, 26 corresponds to a dimension of the notch 8, 26 radially to the nail axis 28. As can be seen, the width of the notch 8, 26 is substantially smaller than a diameter of the through hole 2, e.g. the width of the notch 8, 26 may be approximately a sixth of the diameter of the through hole 2 or less. In choosing the geometry of the notch care should be taken in order not to introduce an excessive additional notch effect. The depth H and the width W of the notch 8, 26 are shown in FIGS. 4a and 4b.

It may be found advantageous to provide a notch 8 as an elongate notch 8 transverse to the nail elongation and to arrange the notch 8 in the proximal half of the rim region 48 as shown in FIGS. 4a and 4b, or in the proximal third of the rim region 48. As can be seen, the notch 8 is intersected by the lateral end of the through hole 2. Further, a plane 44 is indicated, which is substantially perpendicular to the nail axis 28. Thus, the through hole axis 30 is arranged obliquely to the plane 44. A length L of the notch, denominating the longer dimension of the notch may be at least as long as or longer than the diameter of the through hole 2 of the orthopedic nail 10. FIG. 4b shows the orthopedic nail 10 as is indicated in FIG. 4a, however, viewed from the lateral side 4. The notch 8 is perpendicular to the nail axis 28, is perpendicular to the through hole axis 30, and its longitudinal extension is arranged in parallel to the plane 44. Thus, the notch 8 and its notch ground 12 may be of longitudinal shape and extend with its length tangentially to and/or in a direction parallel offset to a tangent to the outer circumferential surface of the orthopaedic nail 10.

The embodiment in FIGS. 5a and 5b shows a notch 8 arranged immediately at the proximal end of the rim region 48. It might prove advantageous while not mandatory in realizing the general idea of this invention to arrange the notch 8 distant from the proximal end of the rim region 48, and thus, to not change the leverage in supporting the momentum induced by the forces acting on the distal part of the lag screw 22.

In one embodiment, the notch 26 is a circumferential notch 26 and runs around the nail 10 as is shown in FIGS. 6a and 6b. On the lateral side 4 of the orthopedic nail 10, the notch 26 is provided in the proximal half of the rim region 48. On the medial side 6 of the orthopedic nail 10, the notch 26 is, in this specific embodiment, provided in a region distally to the medial end of the through hole 2. The circumferential notch 26, in this embodiment, is substantially parallel to the plane 44. Thus, the notch 26 and its notch ground 12 may be of longitudinal shape and extend with its length, in particular curved length, at least partly circumferentially around said outer circumferential surface of the orthopaedic nail 10.

FIGS. 7a and 7b show a further embodiment of the orthopedic nail 10. In this case, two notches 8 are provided on the lateral side 4 of the orthopedic nail 10. The more proximal one of the two notches 8 is situated at or close to the proximal end of the lateral end of the through hole 2, and the more distal one of the two notches 8 is provided at or close to the distal end of the lateral end of the through hole 2. This completely isolates the critical rim region 48 from the rest of the nail 10 with respect to stress components in the axial direction of the nail and thus effectively prevents the rim region 48 from being charged with tensile or pressure stress in a direction parallel to the nail axis.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

LIST OF REFERENCE NUMERALS 2 through hole
4 lateral side
6 medial side
8 notch
10 intramedullary nail
12 notch ground
18 proximal end
22 bone screw
26 circumferential notch
28 nail axis
30 through hole axis
34 proximal end of bone screw
36 threaded portion of bone screw
38 distal end of bone screw
40 intramedullary nail system
44 plane
46 force lines
48 rim region
50 femur
52 fracture
54 femoral neck
58 femoral head
H Depth
L Length
W Width

The invention claimed is:

1. An orthopedic nail of generally rod-like shape having a through hole in a proximal part of said orthopedic nail extending from a first, lateral side to a second, medial side of said orthopedic nail, wherein a lateral end of said through hole is located closer to a distal end of said orthopedic nail than a medial end of said through hole, and being adapted to receive a screw and/or a pin, a first end of said through hole at said first, lateral side defining a rim region, wherein at least one surface notch is provided in said rim region at and restricted to an outer circumferential surface of said orthopaedic nail, said surface notch being arranged transverse to a nail axis of said orthopedic nail, a width (W) of said surface notch in the direction of said nail axis being smaller than a diameter of said through hole, the width being measured in the axial direction of the nail between a proximal most point and a distal most point of said surface notch, wherein a length of said surface notch is longer than said diameter of said through hole, wherein said surface notch is suited to interrupt tensile stress lines in said rim region induced by a force ($F_L$) acting on a support point for said screw and/or pin at said first side in a proximal region of said first end of said through hole.

2. The orthopedic nail in accordance with claim 1, wherein, when viewed from said first side, a depth (H) of said surface notch along the viewing direction and terminating in a notch ground is smaller than the diameter of said orthopaedic nail.

3. The orthopedic nail in accordance with claim 1, wherein said surface notch is intersected by said first end of said through hole.

4. The orthopedic nail in accordance with claim 1, wherein said surface notch is of longitudinal shape.

5. The orthopedic nail in accordance with claim 1, wherein said surface notch is arranged in parallel to a plane which is at least substantially perpendicular to said nail axis.

6. The orthopedic nail in accordance with claim 1, wherein said surface notch is arranged at least substantially perpendicular to a through hole axis of said through hole and/or is arranged at least substantially perpendicular to said nail axis.

7. The orthopedic nail in accordance with claim 1, wherein said width (W) of said surface notch is smaller than a radius of said through hole.

8. The orthopedic nail in accordance with claim 1, wherein said surface notch is positioned in a proximal part of said rim region towards a proximal end of said orthopedic nail away from a hole axis of said through hole.

9. The orthopedic nail in accordance with claim 1, wherein said surface notch is provided at a proximal end of said rim region.

10. The orthopedic nail in accordance with claim 1, wherein said surface notch is provided distant from a proximal end of said rim region.

11. The orthopedic nail in accordance with claim 1, wherein at least two surface notches are provided in said rim region.

12. The orthopedic nail in accordance with claim 11, wherein a first surface notch is positioned in a proximal half of said rim region, and a second surface notch is positioned in a distal half of said rim region.

13. The orthopedic nail in accordance with claim 11, wherein a first surface notch is provided at a proximal end of said rim region and/or a second surface notch is provided at a distal end of said rim region.

14. The orthopedic nail in accordance with claim 1, wherein said orthopedic nail is an intramedullary nail adapted for use within a bone having a medullary channel and/or wherein said surface notch is provided on the first, lateral side of said orthopedic nail.

15. An orthopedic nail system including an orthopedic nail in accordance with claim 1 and a screw and/or a pin, wherein said screw and/or pin are adapted to be received in said through hole of said orthopedic nail and are adapted for the treatment of bone fractures.

16. An orthopedic nail of generally rod-like shape having a through hole in a proximal part of said orthopedic nail extending from a first, lateral side to a second, medial side of said orthopedic nail, wherein a lateral end of said through hole is located closer to a distal end of said orthopedic nail than a medial end of said through hole, and being adapted to receive a screw and/or a pin, a first end of said through hole at said first, lateral side defining a rim region, wherein at least one surface notch is provided in said rim region at and restricted to an outer circumferential surface of said orthopaedic nail, said surface notch being arranged transverse to a nail axis of said orthopedic nail, a width (W) of said surface notch in the direction of said nail axis being smaller than a diameter of said through hole, the width being measured in the axial direction of the nail between a proximal most point and a distal most point of said surface notch, wherein a length of said surface notch is longer than said diameter of said through hole, wherein said surface notch is provided as at least one circumferential surface notch around a circumference of said orthopedic nail, and wherein said circumferential surface notch is provided in a plane that is at least substantially perpendicular to said nail axis or said circumferential surface notch is provided in a plane oblique to said nail axis.

* * * * *